United States Patent [19]

Headley et al.

[11] Patent Number: 5,405,308

[45] Date of Patent: Apr. 11, 1995

[54] DISPOSABLE CENTRIFUGE ROTOR AND CORE FOR BLOOD PROCESSING

[75] Inventors: Thomas D. Headley, Wellesley; Jacques Chammas, Dedham, both of Mass.

[73] Assignee: Haemonetics Corporation, Braintree, Mass.

[21] Appl. No.: 200,909

[22] Filed: Feb. 22, 1994

Related U.S. Application Data

[63] Continuation of Ser. No. 959,751, Oct. 13, 1992, abandoned.

[51] Int. Cl.⁶ .............................................. B04B 1/02
[52] U.S. Cl. ........................................ 494/67; 494/41; 494/43
[58] Field of Search ................ 494/41, 43, 50, 65, 494/67–69, 74, 901

[56] References Cited

U.S. PATENT DOCUMENTS

| | | | |
|---|---|---|---|
| 560,632 | 5/1896 | Peck | 494/50 |
| 560,633 | 5/1896 | Peck | 494/50 |
| 560,634 | 5/1896 | Peck | 494/50 |
| 1,014,849 | 1/1912 | Richardson | 494/41 |
| 1,483,929 | 2/1924 | Coleman | 494/74 |
| 2,551,815 | 5/1951 | Schulz | 494/65 |
| 2,862,658 | 12/1958 | Dahlgren | 494/901 |
| 4,300,717 | 11/1981 | Latham | 494/41 |
| 4,943,273 | 7/1990 | Pages | 494/41 |
| 4,983,158 | 1/1991 | Headley | 494/41 |

FOREIGN PATENT DOCUMENTS

39843 3/1932 France .

Primary Examiner—David A. Scherbel
Assistant Examiner—Terrence R. Till
Attorney, Agent, or Firm—Cesari and McKenna

[57] ABSTRACT

An improved centrifuge rotor formed of a bowl body and core for blood processing applications, such as cell washing or pheresis, is described. A tubular core adapted to rotate with the rotor defines a processing region between the core and the interior of the bowl body. A plurality of projections extend into the processing region to minimize formation of fluid Coriolis waves which would otherwise cause undesirable turbulence.

7 Claims, 2 Drawing Sheets

DISPOSABLE CENTRIFUGE ROTOR AND CORE FOR BLOOD PROCESSING

This application is a continuation of application Ser. No. 07/959,751, filed Oct. 13, 1992, now abandoned.

This invention relates to blood processing and, more specifically, centrifuge bowls and cores for blood processing.

BACKGROUND OF THE INVENTION

Disposable centrifuge bowls have been developed for processing anticoagulated whole blood in pheresis, deglycerolization and cell washing procedures. Prior to about 1986, commercially available disposable blood processing centrifuge bowls were of the type generally shown in FIGS. 1 or 6 of U.S. Pat. No. 4,300,717 (hereinafter "Latham bowl"), or U.S. Pat. No. 4,086,924 (hereinafter "Grenade-type bowl"), [each of which is incorporated herein in their entirety by reference]. The overall bowl construction in each case was similar and consisted of three essential units. The first unit is a multi-piece feed tube and seal assembly, which enables fluids, such as, anticoagulated whole blood and/or wash solution, to be introduced from a fixed location to the interior of a rotating bowl body and processed blood component to be removed from the bowl body and returned to a patient or donor, or stored.

The second unit is comprised of a two-piece bowl body welded together at a peripheral seam.

The third unit is a core usually of fairly solid construction. The core serves a number of functions. In the Latham bowl, the core provides a narrow bottom fluid channel between the base of the core and the bottom of the bowl, through which fluid, admitted through a central feed tube, is passed to the outer periphery of the bowl body interior. In passing through this narrow channel, "impeller" vanes, formed on the bottom of the bowl, imparted rotational velocity to the incoming feed fluid. With the core design shown in the Latham bowl, fluid feed is forced to pass to the outer separation region between the inner peripheral bowl body wall and the outer peripheral wall of the core. From the outer wall, the fluid then must flow inside to reach the effluent port. Without this core design, it would be possible for fluid admitted at the bottom of the bowl to by-pass the processing region and pass directly from the feed tube upwardly through the space between the inner core wall and the feed tube out the effluent port formed between the skirts of the seal assembly. The rigid core body was considered essential to avoid or dampen fluid wave vibrations which might occur between the rotating sterile air in the central region between the core and the feed tube and the fluid processed in the outer separation region.

The Grenade bowl construction is similar, except that the middle bowl body side walls are not tapered and the bottom of the core is not flared. Also, the core of the Grenade-type bowl does not force input feed fluid out to the periphery. Thus, fluid flows from the inside-out in the processing region.

Sometime during 1986/87, a new centrifuge bowl became commercially available. The construction of this bowl is shown in the FIGS. 4–6 embodiment of U.S. Pat. No. 4,983,158 (hereinafter the "Headley bowl" and incorporated herein in its entirety by reference). This new bowl differed from the prior art bowl by the use of a one-piece integral blow molded bowl body.

The FIGS. 4–6 embodiment of the Headley bowl utilized a one-piece core body with an outer diameter equal to or smaller than the opening into the bowl. The small core size, as in the Grenade-type bowl, is insufficient to enable the core to force feed fluid, entering the bottom of the bowl through the feed tube, to be diverted to the extreme outer periphery of the processing region between the core body and the bowl wall. This diversion is important for cell washing applications.

In cell washing systems, shed blood from a patient is filtered, collected and washed with saline in a disposable centrifuge bowl. Anticoagulated, filtered shed whole blood enters at the bottom center of the bowl and is separated by centrifugal forces into more dense red cells and less dense other components. The red cells fill the outermost portion of the rotating centrifuge bowl. As more shed blood enters the bowl, the red cells remain in the bowl displacing the supernatant (saline, plasma, contaminants, etc.) out of the mid-central region of the bowl. This concentrates the red blood cells in the bowl. Next, saline is directed into the bottom of the bowl, instead of shed blood. Saline, entering the Latham bowl, is directed by the lower extended skirt portion of the core to the outermost radius of the bowl and through the bed of packed red blood cells. In this way, the supernatant is diluted and displaced by the saline until a satisfactory amount of non-red blood cell fluid, i.e., plasma, anticoagulant and contaminants, originally entering the bowl, are removed by the wash process. The centrifugal washing procedure in conjunction with filtration concentrates the red blood cells and removes contaminants, such as blood clots, bone chips, fatty tissue and activated clotting factors. The patient can then be reinfused with his or her own washed red blood cells.

The referenced Headley bowl lacks a diverter structure, as in the Latham-type bowl. Therefore, some of the saline wash solution may not be forced to travel to the extreme outer periphery before exiting the bowl through the effluent skirts on the rotary seal. This substantially decreases the cell washout efficiency and, hence, the time it takes to complete a cell washing procedure.

In the FIG. 7 and FIGS. 9–10 embodiments of the Headley bowl and in the bowl of U.S. Pat. No. 4,943,273 (hereinafter the "Pages bowl"), [and incorporated herein in its entirety by reference], core structures are disclosed which permit use of an integral bowl body, while providing a diverter structure.

In one embodiment, the core is formed of one-piece construction using semi-rigid plastic material with a flared core and a wall body which can be deflected to allow the flared core to be inserted through the smaller diameter opening (FIG. 7 of the Headley bowl patent).

In another embodiment, the core is of two-piece construction. One piece is comprised of a generally cylindrical hollow walled core. The other piece is a disc-like member with a flared wall portion adapted to be located adjacent the diagonal wall of the bowl body (FIGS. 9–10 of the Headley bowl patent).

In the embodiment of the Pages bowl patent, the core assembly consists of two plastic pieces made by injection molding or similar processes. The first piece is a generally cylindrical rigid hollow-walled core, similar to the walled core in the parent application. The second piece is a diverter in the form of a semi-rigid donut-like member, scalloped at its peripheral edges and having an outer diameter greater than the bowl opening and about equal to the inner diameter of the mid-section of the bowl.

An inner hole is provided on the donut-like member. This hole has a diameter slightly smaller than the diameter of the skirt of the effluent tube.

DISCLOSURE OF THE INVENTION

The invention comprises a blood processing centrifuge rotor having a rotatable bowl body, a rotary seal and a core assembly. The bowl body is provided with an aperture concentric to a longitudinal axis of rotation of the body. The rotary seal seals the aperture and provides fluid communication into and out of the interior of the bowl body. The core assembly is of two-piece construction, consisting of a core and a diverter. The core is generally cylindrical in shape, with the cylinder defining a processing region between it and the inner periphery of the bowl body.

As a cell or particle in a rotating fluid travels radially inwardly or outwardly in the separation chamber, the angular momentum of the cell or particle must be conserved. If the radius of rotation is changing and the angular momentum must be conserved, the angular velocity must go up or down to compensate. This imparts a Coriolis velocity to the cell or particle and this results in different layers of cells or particles moving at different velocities relative to each other and the fluid. This, in turn, can result in turbulence which can cause cell damage and spillage of blood out the effluent skirts. In accordance with the invention, the core is provided with projections extending from the core into the processing region. These projections disrupt the above-described flow patterns which tend to arise in the operation of the centrifuge rotor.

The projections are preferably formed integral with the core and extend transverse the axis of rotation of the bowl. The projections disrupt the flow patterns needed to form turbulence waves and increase the drag on any relative circular flow between layers of fluid in the processing region.

BEST MODE FOR CARRYING OUT THE INVENTION

Figure 1:
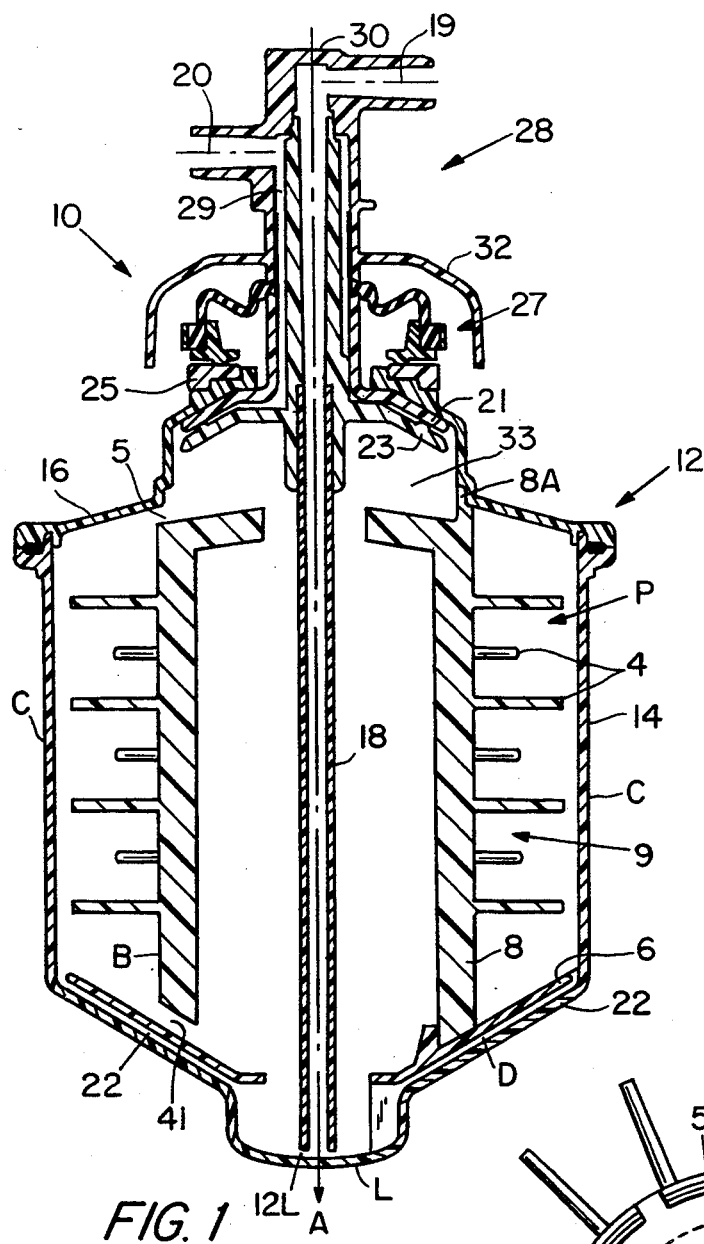
FIG. 1 is a sectional view showing a centrifuge bowl of the present invention.

Referring to FIGS. 1-4, a preferred embodiment of the apparatus of the invention will now be described in detail in connection therewith. It is emphasized that the method and apparatus of the invention is capable of general applicability to a variety of blood processing methods, such as cell washing, pheresis, and to other bowl body structures.

As shown therein, the centrifuge rotor or bowl 10 of the invention, comprises a seal and header assembly, shown generally at 28; a two-piece bowl body, shown generally at 12 and consisting of bowl 14 and cap 16; and a core assembly 9 comprising core 8 and diverter 6.

The seal and header assembly 28 is substantially identical to the seal and header assembly utilized in the Headley bowl referenced above. Briefly, the assembly 28 is comprised of a header 30, which has an inlet bore 19 extending transverse the longitudinal axis "A" of the bowl and then into a longitudinal passageway coupled to the inner bore of the assembly 28. The passageway leads to stem 18 forming an inlet fluid communication path for feed fluid, i.e., anticoagulated whole blood or saline, to enter the interior of centrifuge bowl 12 at the lower longitudinally axial portion 12L of the bowl 12.

Assembly 28 is also provided with an outlet bore 20, which extends transversely into a peripheral channel extending in parallel relationship with the feed tube assembly 28 and into an outlet coaxial passageway 29. A secondary shield 32 is formed on assembly 30 and extends over a rotary seal 27. A pair of complementary skirts 21 and 23 provide an effluent passageway, therebetween, connecting the outlet passageway 29 to the outlet bore 20.

Cap 16 extends coaxially at one end from, and is bonded to, lower seal member 25 and is bonded thereto at its periphery. The other end is crimped and sealed to the periphery of bowl 14 at opening 33 after the core assembly 8 has been inserted into the bowl 14.

The bowl 12 is preferably of two-piece molded construction and may be formed of a suitable plastic, such as transparent styrene or equivalent.

The bowl 14 is formed of a straight middle central portion C extending vertically downward, a lower diagonal portion D extending radially inwardly and downward, and a lower cross portion L. Opening 33 extends longitudinally from the inner surface of the center portion C into the main portion of the bowl 14.

Core 8 is preferably an integral member formed of a suitable rigid, or semi-rigid, blood compatible transparent plastic and has a cylindrical outer wall B extending longitudinally downward and coaxial to the axis A of bowl 14. Drainage holes 41 are provided at the base of the core adjacent diverter 6. An upper transverse ring portion 8A of core 8 is adapted to abut the inner wall of the cap 16 of the bowl body 12.

Peripheral slots (one of which is shown at 5) extend along the periphery of the core body at the juncture between the ring portion 8A and the inner wall of cap 16. These slots provide a passageway for the exit of effluent, such as supernatant or plasma, which has been separated from the packed red blood cells by the operation of the centrifuge cell washing or pheresis process within the bowl body 12.

Figure 3:
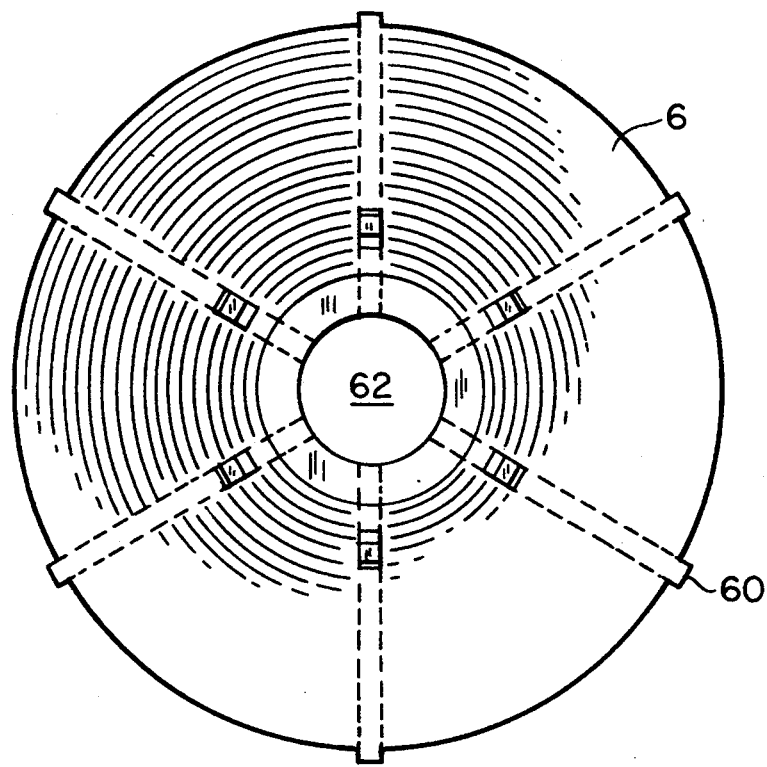
FIG. 3 is a top plan view of the diverter 6 of FIG. 1.
Figure 4:
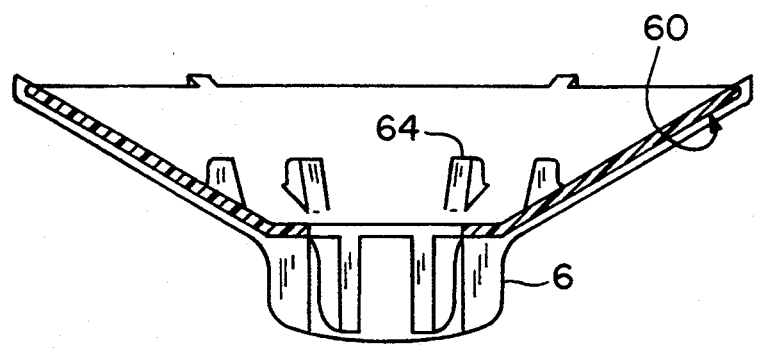
FIG. 4 is a section taken through the center of diverter 6 of FIG. 3.

Diverter 6, as shown in FIGS. 3 and 4, is an annular member formed of blood-compatible rigid or semi-rigid transparent plastic material. Diverter 6 is of molded construction and includes six ribs 60 extending radially from central opening 62. The ribs perform the same impeller function as the vanes in the Latham Bowl previously described. Projections 64 extend vertically to support the periphery of the bottom of core 8, which is abutted thereto.

Core 8 is provided with a plurality of slender projections 4, spaced about the periphery of the cylindrical core wall and extending into the processing region. The function of the projections is to prevent the formation of fluid waves in the processing region at the interface between fluid media. These waves occur due to the Coriolis effect. A Coriolis velocity arises when a cell or particle travels in a radial or circumferential direction within a rotating fluid. As previously noted, cells or particles travel radially inwardly or outwardly in the processing region. The angular momentum of the cell or particle must be conserved. Therefore, the cell particle tends to seek a position in the field that matches its own angular momentum. The radius of rotation is continuously changing as the bowl rotates and the angular momentum must be conserved. Therefore, the angular velocity of the cell or particle must go up or down to compensate. This results in different layers of cells or particles moving at different velocities relative to each other and the surrounding fluid. This, in turn, can result in turbulence which can cause cell damage and/or spillage of blood out the effluent skirts.

The core projections 4, in the form of small spikes, disrupt the flow patterns needed to form waves and increase the drag on any relative circular flow layers of fluid or blood, thereby minimizing or eliminating turbulence.

Preferably, the projections are formed as an integral part of the core wall where the core is formed in a mold. The core and projections may be formed of rigid blood compatible plastic, such as polyethelene, polystyrene and polypropelene.

Various sizes, shapes and locations for the projections are envisioned, depending upon the particular application. The centrifugal speed and bowl fill rate will affect the number of projections needed. In general, the higher the centrifugal speed, the more number of projections are required, whereas the lower the flow rate, the less the number of projections needed. Preferably, the projections are of identical lengths and uniformly spaced.

Figure 5:
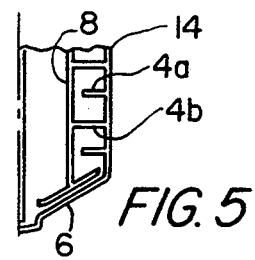
FIG. 5 is a schematic partial cross-section of a first alternate embodiment of the invention.
Figure 6:
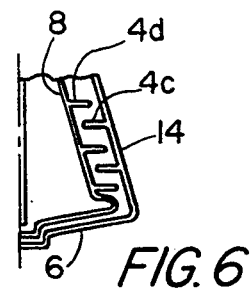
FIG. 6 is a schematic partial cross-section of a second alternate embodiment of the invention.

Various projection geometries are contemplated. FIG. 5 depicts schematically a bowl 14 having interdigitated projections in which some projections 4a are formed on the bowl body per se., while alternate projections 4b are formed on the core 8 and project radially outwardly. Note that the projections 4b may extend from core to bowl body, as shown in FIG. 5, or as shown in the Latham-type bowl of FIG. 6 or the bowl of FIG. 1 may be foreshortened before touching the side of the core (projection 4c) or side of the bowl (projection 4d). Care should be taken to leave sufficient space in either case, so that packed RBC is not lysed by being squeezed between the projections and the sidewalls. A spacing of at least 0.060 inches from a sidewall is recommended. Angular spacing between projections may run from about 22½ degrees to 45 degrees.

Figure 7:
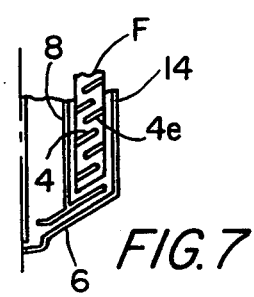
FIG. 7 is a schematic partial cross-section of a third alternate embodiment of the invention.
Figure 2:
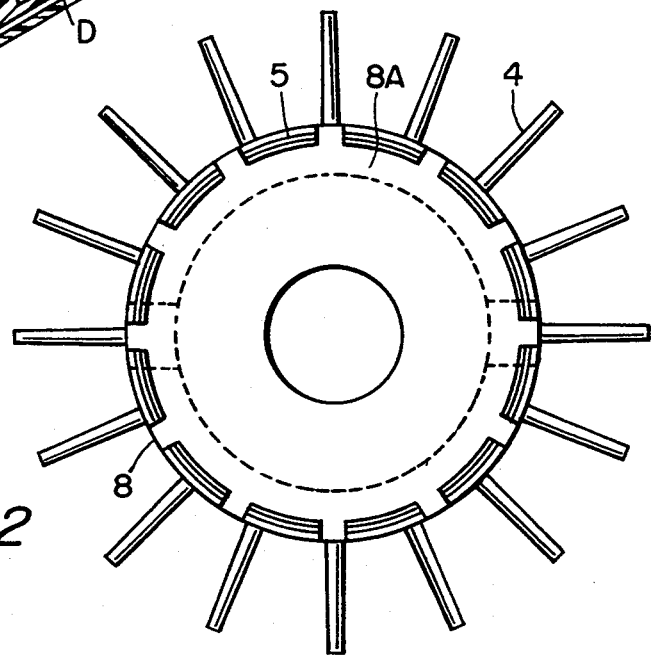
FIG. 2 is a top plan view of the core 8 of FIG. 1.

In the embodiment of FIG. 7, the projections are supported in a separate frame F for insertion in the bowl 14.

The apparatus of the invention is particularly suitable for use in autotransfusion applications. During the process of intraoperative cell salvage and autotransfusion, shed blood and other fluids are typically processed in a disposable centrifuge bowl.

The first function of the centrifuge bowl is to concentrate the blood cells. If the concentration is to be accomplished efficiently, the geometry of the bowl and the resulting fluid flows must promote efficient separation of the cellular components from the other fluids. The second function of the centrifuge bowl is to wash the cells by washing out any unwanted fluids from around the cells. For efficient washing, the geometry of the bowl and the resulting fluid flows must promote efficient mixing of the cellular components with the wash fluids. In other words, the bowl has to sufficiently mix the fluids with the cells in order to wash the cells, while keeping turbulence at a minimum to maintain a good concentration of the cells.

These two functions are accomplished by the bowl body and core assembly construction of the invention, which forces incoming blood and fluids to enter the bowl at the periphery of the bowl through openings 22 provided between diverter 6 and portion D of bowl 14.

Additionally, the spike-like protrusions 4 from the core 8 reduce the turbulence in the processing region P of the bowl. This combination of geometries provides the proper flow patterns and environment so that the bowl can handle high speed filling with blood and high speed and efficient washing of the concentrated cells.

When the bowl is being filled, the bowl is operated at high speed. Good concentration of the cells and low cell spillage is achieved because there is no direct path for the newly entering blood from stem 18 to exit the bowl. The newly entering blood is forced to flow through a wide area D of the processing region P. This increases the residence time of the newly entering blood in the bowl, so there is more time for the centrifugal force to separate the cells from the rest of the fluid. Blood entering at this location would normally generate high turbulence, but the spikes 4 dampen the turbulence out. Therefore, efficient separation is achieved.

Another important application for the bowl is in deglycerolization.

During the process of deglycerolization of red blood cells, a bag of cells is first diluted with a high concentration salt solution to shrink the cells and drive out most of the glycerol. Additionally, dilutions of the cells are made with a low concentration salt solution followed by periods of equilibration to reduce the saline concentration around the cells before pumping the cells into the bowl for washing.

The function of the centrifuge bowl is to wash the cells by continuously reducing the salt concentration of the fluids around the cells. For efficient washing, the geometry of the bowl and the resulting fluid flows must promote efficient mixing of the cellular components with the wash fluids. However, if the mixing becomes too turbulent, the red cells will be washed out of the bowl and lost. The bowl must therefore be capable of sufficiently mixing the fluids with the cells to wash the cells but keep turbulence at a minimum, so a proper concentration of the cells is maintained. These two functions are accomplished by the present invention in which incoming fluids at stem 18 are forced to enter the bowl at the periphery of the bowl through the openings 22 in diverter 6 in such a location that there is no direct flow pathway out of the bowl. Additionally, the spike-like protrusions 4 from the core 8, reduces the turbulence in the processing region of the bowl. This combination of geometries provides the proper flow patterns and environment, so the bowl will handle high speed and efficient washing of the concentrated cells with minimal cell spillage.

Eliminating the Coriolis flow, as described herein, produces a stable buffy coat, reducing cross-contamination of components, making it easier to separate less dense from more dense components.

Equivalents

Those skilled in the art will recognize that there are many equivalents to the specific embodiments shown herein. Accordingly, the invention is not to be limited except as may be required by the scope of the claims herein.

We claim:

1. A blood processing centrifuge rotor, for separating less dense blood components from more dense blood components by centrifugation in a rotor comprising:
   a) a bowl body rotatable about a longitudinal axis with an aperture at one end of the body provided concentric to said axis;
   b) a rotary seal assembly affixed to said bowl body for sealing the aperture and having input and output ports for fluid communication with the interior of said bowl body and a stem for introducing blood fluid to a bottom portion of the bowl body at an end opposite said aperture and effluent skirts in fluid communication with said output port;
   c) a core having a tubular wall, rotatable with said bowl body about said longitudinal axis and extending into the bowl body to form a blood fluid processing region between the core and the bowl body in which blood fluid flows in patterns and is separated into fluid components and displaced upwardly to said effluent skirts; and
   d) means projecting from the wall into the processing region for disrupting said patterns and minimizing turbulence and blood component damage.

2. The rotor of claim 1 including an annular diverter affixed to said core for forcing fluid entering said bowl body at the axis to pass to the inner periphery of the bowl body.

3. The rotor of claim 1 wherein the projections extend radially inward from the bowl body.

4. The rotor of claim 1 wherein the projections extend from the core to the bowl body.

5. The rotor of claim 1 wherein some of the projections extend from the core toward the body and some extend from the body to the core.

6. Apparatus for separating less dense blood components from more dense blood components by centrifugation in a rotor, comprising:
   a) a centrifuge bowl having an aperture at an upper end thereof and a rotary seal sealing said aperture including input and output ports with an effluent skirt coupled to said output port and in which whole blood fluid is introduced through said input port to a lower end thereof into a central region of a blood fluid centrifugation chamber having an inner longitudinally extending core, said core and chamber joined together and rotatable together about a central axis causing the whole blood to separate in a space between the outer periphery of the chamber and core in accordance with the density of the blood components and wherein the separated whole blood components are displaced upwardly, such that the more dense components tend to locate at the outer periphery of the chamber and whereby blood components are imparted with a Coriolis velocity which tends to form blood fluid waves; and
   b) means projecting between said core and outer periphery for disturbing the formation of such blood fluid waves and minimize turbulence within said space and damage to said separated components.

7. The apparatus of claim 6 including a tube coupled to the input port and extending along the central axis to the region of the bowl opposite the seal.

* * * * *